(12) United States Patent
Altmann et al.

(10) Patent No.: US 11,540,877 B2
(45) Date of Patent: Jan. 3, 2023

(54) PULSE GENERATOR FOR IRREVERSIBLE ELECTROPORATION

(71) Applicant: BIOSENSE WEBSTER (ISRAEL) LTD., Yokneam (IL)

(72) Inventors: Andres Claudio Altmann, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 244 days.

(21) Appl. No.: 16/701,989

(22) Filed: Dec. 3, 2019

(65) Prior Publication Data

US 2021/0161592 A1    Jun. 3, 2021

(51) Int. Cl.
*A61B 18/12* (2006.01)
*A61B 18/14* (2006.01)
(Continued)

(52) U.S. Cl.
CPC ...... *A61B 18/1492* (2013.01); *A61B 18/1206* (2013.01); *A61B 2017/00154* (2013.01);
(Continued)

(58) Field of Classification Search
CPC ............ A61B 18/1492; A61B 18/1206; A61B 2017/00154; A61B 2018/00363; A61B 2018/00577; A61B 2018/00613; A61B 2018/00821; A61B 2018/126; A61B 2018/1467; A61B 2018/00839; A61B 2018/00642; A61B 2018/124
See application file for complete search history.

(56) References Cited

U.S. PATENT DOCUMENTS

| 8,048,067 B2 | 11/2011 | Davalos |
| 8,221,411 B2 | 7/2012 | Francischelli |

(Continued)

FOREIGN PATENT DOCUMENTS

| CN | 107921258 | 4/2018 |
| CN | 110234290 | 9/2019 |

(Continued)

OTHER PUBLICATIONS

Vivek Y. Reddy, MD et al., "Pulsed Field Ablation for Pulmonary Vein Isolation in Atrial Fibrillation", Journal of the American College of Cardiology, vol. 74, No. 3, 2019.

(Continued)

*Primary Examiner* — Jaymi E Della
(74) *Attorney, Agent, or Firm* — Dergosits & Noah LLP; Todd A. Noah

(57) ABSTRACT

A medical apparatus includes a probe configured for insertion into a body of a patient. The probe includes a plurality of electrodes configured to contact tissue within the body. The medical apparatus further includes an electrical signal generator configured to apply between one or more pairs of the electrodes signals of first and second types in alternation. The signals of the first type include a sequence of bipolar pulses having an amplitude sufficient to cause irreversible electrophoresis (IRE) in the tissue contacted by the electrodes. The signals of the second type include a radiofrequency (RF) signal having a power sufficient to thermally ablate the tissue contacted by the electrodes.

42 Claims, 8 Drawing Sheets

(51) Int. Cl.
  *A61B 34/20* (2016.01)
  *A61B 17/00* (2006.01)
  *A61B 18/00* (2006.01)
  *A61B 18/16* (2006.01)

(52) U.S. Cl.
  CPC ............ *A61B 2017/00199* (2013.01); *A61B 2018/00363* (2013.01); *A61B 2018/00577* (2013.01); *A61B 2018/00613* (2013.01); *A61B 2018/00642* (2013.01); *A61B 2018/00821* (2013.01); *A61B 2018/00839* (2013.01); *A61B 2018/124* (2013.01); *A61B 2018/126* (2013.01); *A61B 2018/1467* (2013.01); *A61B 2018/167* (2013.01); *A61B 2034/2051* (2016.02)

(56) References Cited

U.S. PATENT DOCUMENTS

| | | | |
|---|---|---|---|
| 9,877,781 | B2 | 1/2018 | Grasse |
| 10,271,893 | B2 | 4/2019 | Stewart |
| 10,342,598 | B2 | 7/2019 | Long |
| 10,531,914 | B2 | 1/2020 | Stewart et al. |
| 2010/0023004 | A1* | 1/2010 | Francischelli ..... A61B 18/1442 606/41 |
| 2014/0066913 | A1* | 3/2014 | Sherman ............ A61B 18/1492 606/20 |
| 2015/0182740 | A1* | 7/2015 | Mickelsen ........... A61B 5/0538 604/506 |
| 2016/0051324 | A1 | 2/2016 | Stewart |
| 2016/0184003 | A1 | 6/2016 | Srimathveeravalli |
| 2016/0331441 | A1 | 11/2016 | Konings |
| 2017/0035499 | A1* | 2/2017 | Stewart .............. A61B 18/1492 |
| 2017/0065340 | A1* | 3/2017 | Long .................. A61B 18/1492 |
| 2017/0143414 | A1 | 5/2017 | Sliwa et al. |
| 2017/0333109 | A1* | 11/2017 | Gilbert ............... A61B 18/1206 |
| 2017/0348525 | A1 | 12/2017 | Sano |
| 2018/0214202 | A1 | 8/2018 | Howard et al. |
| 2019/0038337 | A1 | 2/2019 | Schoenbach |
| 2019/0143106 | A1 | 5/2019 | Dewitt |
| 2019/0336207 | A1 | 11/2019 | Viswanathan |

FOREIGN PATENT DOCUMENTS

| | | | |
|---|---|---|---|
| EP | 1157667 A2 * | 11/2001 | ......... A61B 18/1233 |
| WO | 2018200800 A1 | 11/2018 | |

OTHER PUBLICATIONS

Nebojsa Mujovic et al., "Catheter Ablation of Atrial Fibrillation: An Overview for Clinicians", Adv. Ther. 34: 1897-1917, 2017.
World Health Organization Study: Atrial Fibrillation is a Growing Global Health Concern, Dec. 17, 2013.
PCT International Search report for corresponding patent application No. PCT/IP2020/050680 dated Jul. 30, 2020.
Office Action from corresponding Chinese Patent Application No. 2020110202430 dated May 25, 2021.
Search Report from corresponding European Patent Application No. 20211214.0 dated Apr. 6, 2021.

* cited by examiner

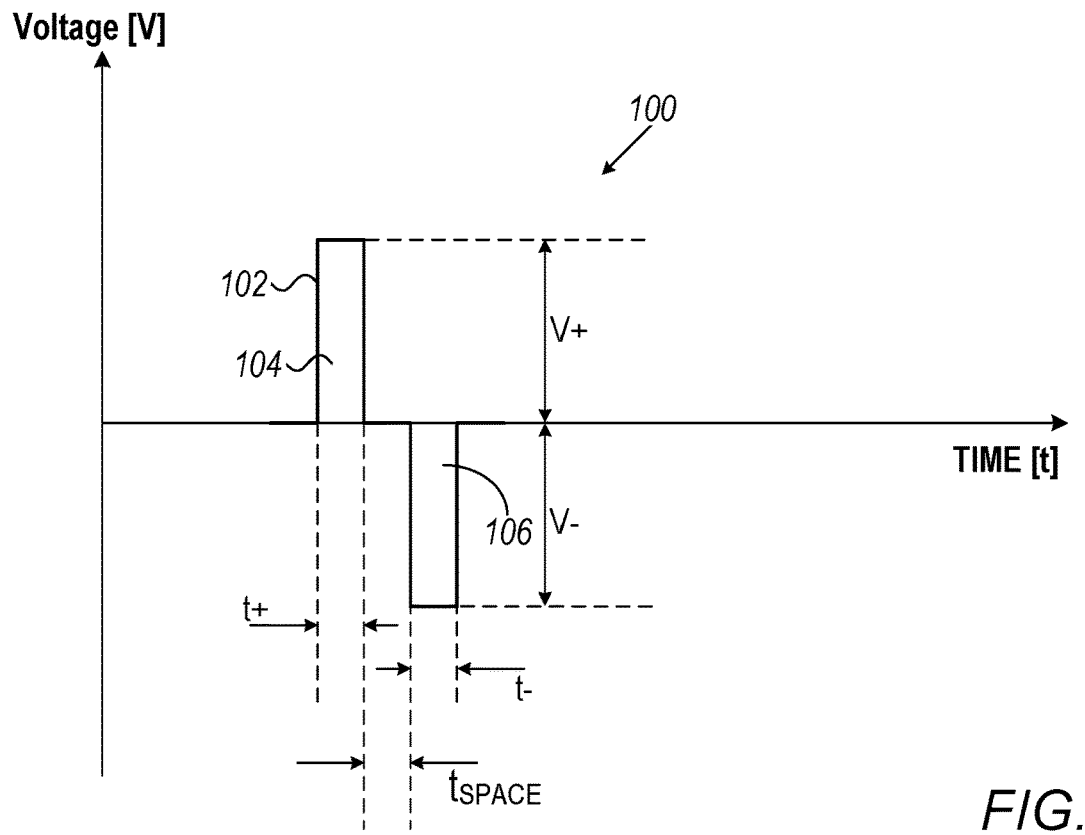
FIG. 2
FIG. 3
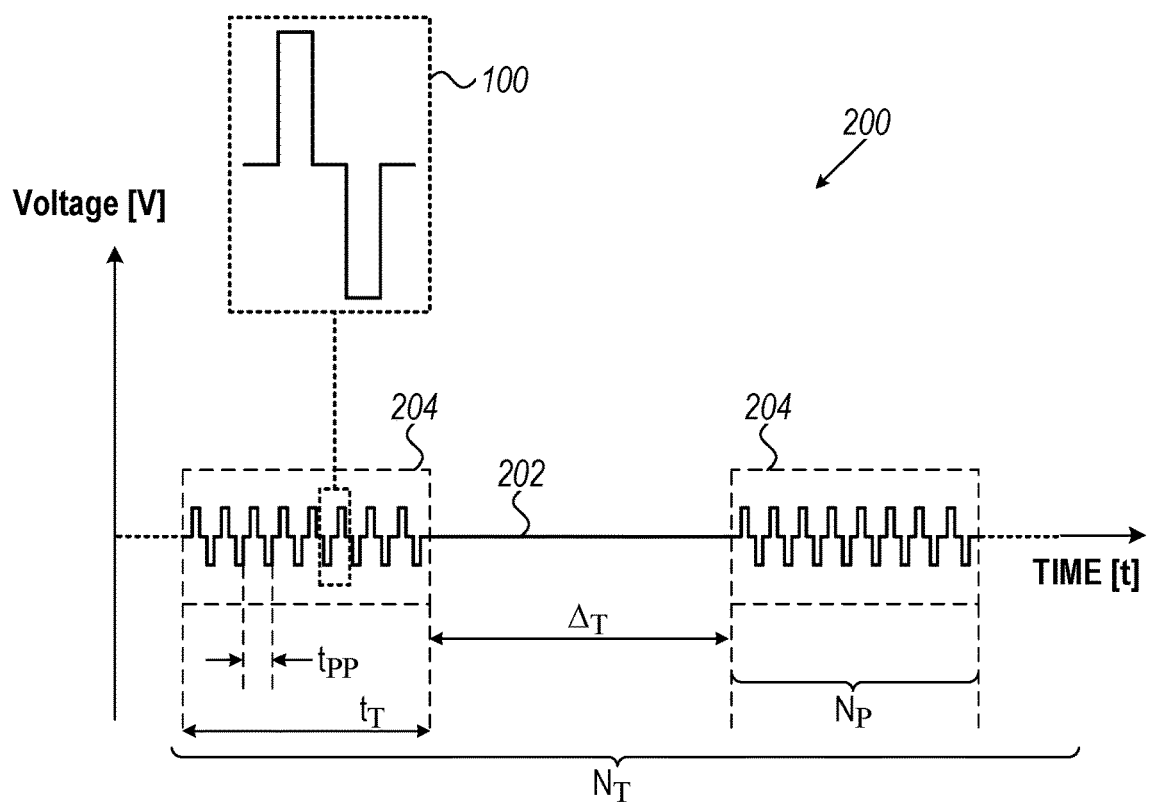

PULSE GENERATOR FOR IRREVERSIBLE ELECTROPORATION

FIELD OF THE INVENTION

The present invention relates generally to medical equipment, and particularly to apparatus and methods for irreversible electroporation (IRE).

BACKGROUND

Irreversible electroporation (IRE) is a soft tissue ablation technique that applies short pulses of strong electrical fields to create permanent and hence lethal nanopores in the cell membrane, thus disrupting the cellular homeostasis (internal physical and chemical conditions). Cell death following IRE results from apoptosis (programmed cell death) and not necrosis (cell injury, which results in the destruction of a cell through the action of its own enzymes) as in all other thermal or radiation based ablation techniques. IRE is commonly used in tumor ablation in regions where precision and conservation of the extracellular matrix, blood flow and nerves are of importance.

SUMMARY

Exemplary embodiments of the present invention that are described hereinbelow provide improved systems and methods for irreversible electroporation.

There is therefore provided, in accordance with an exemplary embodiment of the present invention, a medical apparatus, which includes a probe configured for insertion into a body of a patient and which includes a plurality of electrodes configured to contact tissue within the body, and an electrical signal generator configured to apply between one or more pairs of the electrodes signals of first and second types in alternation. The signals of the first type include a sequence of bipolar pulses having an amplitude sufficient to cause irreversible electroporation (IRE) in the tissue contacted by the electrodes, and the signals of the second type include a radio-frequency (RF) signal having a power sufficient to thermally ablate the tissue contacted by the electrodes.

In a disclosed exemplary embodiment, the electrical signal generator is further configured to apply the signals of the first type without the alternation with the signals of the second type. Additionally or alternatively, the electrical signal generator is configured to apply the signals of the second type without the alternation with the signals of the first type.

In some exemplary embodiments, the sequence of bipolar pulses includes pulses having an amplitude of at least 200 V, and a duration of each of the bipolar pulses is less than 20 μs. Additionally or alternatively, the RF signal has a frequency between 350 and 500 kHz and an amplitude between 10 and 200 V.

In some exemplary embodiments, the medical apparatus includes a controller configured to transmit control signals to the electrical signal generator. The electrical signal generator includes a pulse generation assembly, configured to receive the control signals from the controller and to transmit sequences of bipolar pulses with an amplitude and duration responsive to the control signals. The electrical signal generator further includes a pulse routing and metrology assembly, which includes a configurable network of multiple, mutually connected fast switches and slow relays, which are configured to receive the control signals from the controller, to receive the sequences of bipolar pulses from the pulse generation assembly, and to transmit the sequences of bipolar pulses to the plurality of electrodes responsively to the received control signals. In a disclosed exemplary embodiment, the electrical signal generator includes a low-pass filter, which is configured to receive and filter a pulse train from the pulse generation assembly so as to convert the pulse train to the RF signal, thereby generating the signals of the second type.

In a disclosed exemplary embodiment, the signals of the first type include pairs of pulses, where each pair includes a positive pulse and a negative pulse, and where the signals of the second type are interleaved between the positive and negative pulses of the pairs. Alternatively, the signals of the second type are interleaved between successive pairs of the pulses.

In some exemplary embodiments, the electrical signal generator is configured to generate a plurality of pulse trains, wherein each pulse train includes the signals of the first and second types, and wherein the pulse trains are separated by intervals in which the signals are not applied.

In a further exemplary embodiment, the probe includes a plurality of temperature sensors adjacent to the electrodes, and the electrical signal generator is configured to apply the signals responsively to a temperature measured by the temperature sensors.

In a disclosed exemplary embodiment, the probe is configured to contact the tissue in a heart of the patient and to apply the signals so as to ablate the tissue in the heart. In one exemplary embodiment, the electrical signal generator is configured to apply the signals asynchronously with respect to a beating of the heart. Alternatively, the electrical signal generator is configured to apply the signals synchronously with respect to a beating of the heart.

In another exemplary embodiment, the electrical signal generator is configured to apply, during a first period of time while the probe contacts a locus in the tissue, between each electrode and a first neighboring electrode on a first side of the electrode in the array, a first sequence of the bipolar pulses having an amplitude sufficient to cause irreversible electroporation (IRE) in the tissue between each electrode and the first neighboring electrode. The electrical signal generator is further configured to apply during a second period of time while the probe remains in contact with the locus in the tissue, between each electrode and a second neighboring electrode on a second side of the electrode, opposite the first side, in the array, a second sequence of the bipolar pulses capable of causing IRE in the tissue between the electrode and the second neighboring electrode.

There is also provided, in accordance with an exemplary embodiment of the present invention, a medical apparatus, including a probe configured for insertion into a body of a patient, wherein the probe includes an array of electrodes disposed along the probe and configured to contact tissue within the body. An electrical signal generator is configured to apply during a first period of time while the probe contacts a locus in the tissue, between each electrode and a first neighboring electrode on a first side of the electrode in the array, a first sequence of bipolar pulses having an amplitude sufficient to cause irreversible electroporation (IRE) in the tissue between each electrode and the first neighboring electrode. The electrical signal generator is further configured to apply during a second period of time while the probe remains in contact with the locus in the tissue, between each electrode and a second neighboring electrode on a second side of the electrode, opposite the first side, in the array, a second sequence of bipolar pulses capable of causing IRE in the tissue between the electrode and the second neighboring electrode.

In a disclosed exemplary embodiment, the electrical signal generator is further configured to apply sequences of the bipolar pulses between pairs of electrodes that are separated by at least one other electrode in the array, with an amplitude sufficient to cause irreversible electroporation (IRE) in the tissue between the electrodes in the pairs.

There is additionally provided, in accordance with an exemplary embodiment of the present invention, a method for ablating tissue within a body of a patient. The method includes inserting a probe into the body, wherein the probe includes a plurality of electrodes configured to contact the tissue. The method further includes applying between one or more pairs of the plurality of electrodes signals of first and second types in alternation. The signals of the first type include a sequence of bipolar pulses having an amplitude sufficient to cause irreversible electroporation (IRE) in the tissue contacted by the electrodes, and the signals of the second type include a radio-frequency (RF) signal having a power sufficient to thermally ablate the tissue contacted by the electrodes.

There is further provided, in accordance with an exemplary embodiment of the present invention, a method for ablating tissue within a body of a patient. The method includes inserting a probe into the body, wherein the probe includes a plurality of electrodes disposed along the probe and configured to contact the tissue. The method further includes applying during a first period of time while the probe contacts a locus in the tissue, between each electrode and a first neighboring electrode on a first side of the electrode in the array, a first sequence of bipolar pulses having an amplitude sufficient to cause irreversible electroporation (IRE) in the tissue between each electrode and the first neighboring electrode. During a second period of time while the probe remains in contact with the locus in the tissue, a second sequence of bipolar pulses capable of causing IRE in the tissue is applied between each electrode and a second neighboring electrode on a second side of the electrode, opposite the first side, in the array.

BRIEF DESCRIPTION OF THE DRAWINGS

The present invention will be more fully understood from the following detailed description of the embodiments thereof, taken together with the drawings in which:

FIG. 2 is a schematic illustration of a bipolar IRE pulse, in accordance with an exemplary embodiment of the present invention;

FIG. 3 is a schematic illustration of a burst of bipolar pulses, in accordance with an exemplary embodiment of the present invention;

DETAILED DESCRIPTION OF EMBODIMENTS

Overview

Figure 1:
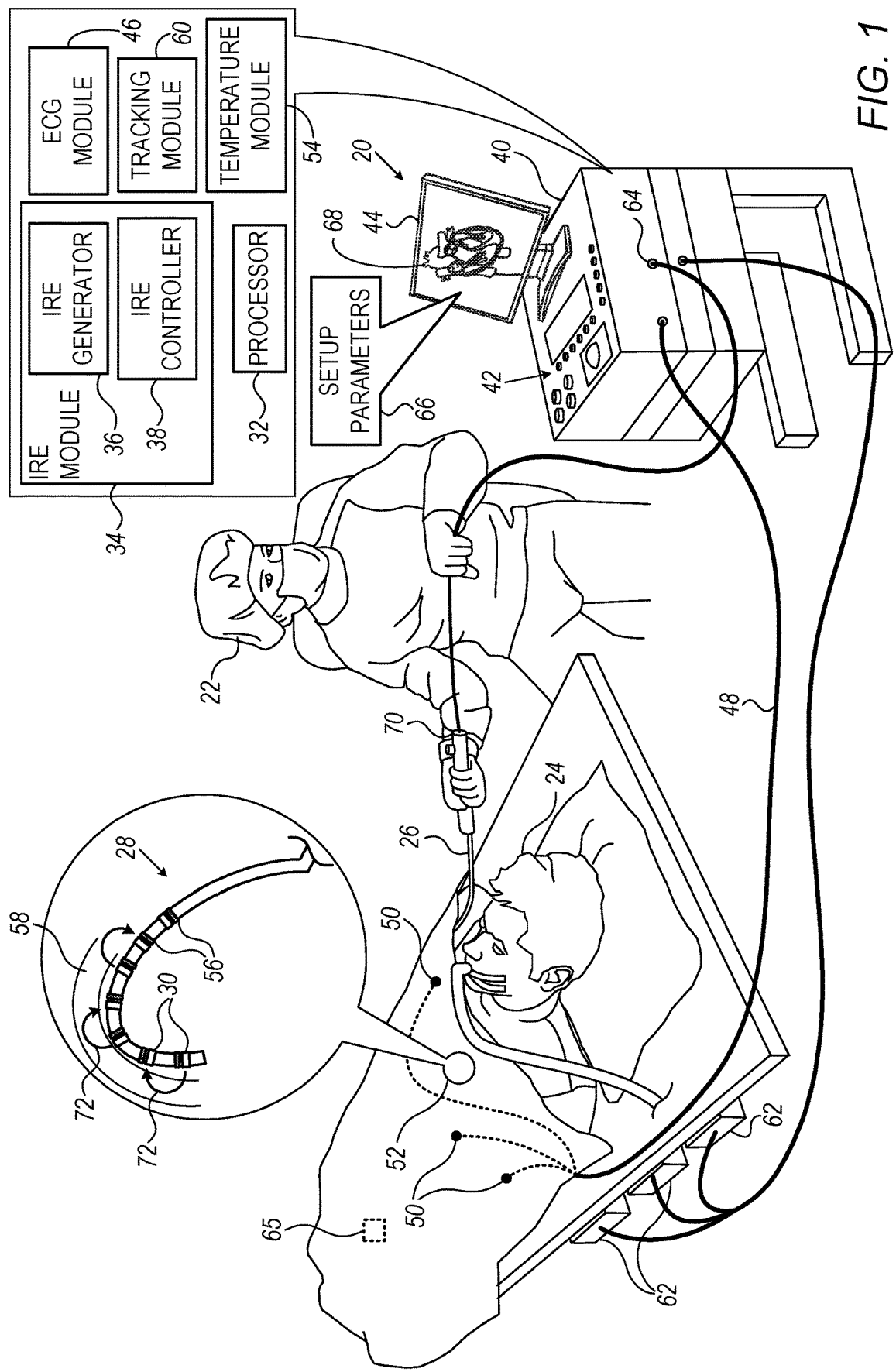
FIG. 1 is a schematic pictorial illustration of a multi-channel IRE system used in an IRE ablation procedure, in accordance with exemplary embodiments of the present invention.

IRE is a predominantly non-thermal process, which causes an increase of the tissue temperature by, at most, a few degrees for a few milliseconds. It thus differs from RF (radio frequency) ablation, which raises the tissue temperature by between 20 and 70° C. and destroys cells through heating. IRE utilizes bipolar pulses, i.e., combinations of positive and negative pulses, in order to avoid muscle contraction from a DC voltage. The pulses are applied, for example, between two bipolar electrodes of a catheter.

In order for the IRE-pulses to generate the required nanopores in tissue, the field strength E of the pulses must exceed a tissue-dependent threshold Eth. Thus, for example, for heart cells the threshold is approximately 500 V/cm, whereas for bone it is 3000 V/cm. These differences in threshold field strengths enable IRE to be applied selectively to different tissues. In order to achieve the required field strength, the voltage to be applied to a pair of electrodes depends both on the targeted tissue and on the separation between the electrodes. The applied voltages may reach up to 2000 V, which is much higher than the typical voltage of 10-200 V in thermal RF ablation.

A bipolar IRE-pulse comprises a positive and a negative pulse applied between two electrodes with pulse widths of 0.5-5 µs and a separation between the positive and negative pulses of 0.1-5 µs. Herein the terms "positive" and "negative" refer to an arbitrarily chosen polarity between the two electrodes. The bipolar pulses are assembled into pulse trains, each train comprising between one and a hundred bipolar pulses, with a pulse-to-pulse period of 1-20 µs. To perform IRE ablation at a given location, between one and a hundred pulse trains are applied between a pair of electrodes at the location, with a spacing between consecutive pulse trains of 0.3-1000 ms. The total energy per channel (electrode-pair) delivered in one IRE ablation is typically less than 60 J, and an ablation may last up to 10 s.

When a multi-electrode catheter is used in an IRE procedure, successive pairs of electrodes may be cycled through during the procedure. Taking as an example a 10-electrode catheter, the electrode pairs may be energized in an adjacent fashion (1-2, 2-3, . . . 9-10) or in an interleaved fashion (1-3, 2-4, . . . 8-10). However, energizing, for example, adjacent pairs must be done in two stages, first energizing the odd-even electrodes 1-2, 3-4, 5-6, 7-8 and 9-10, and then the even-odd electrodes 2-3, 4-5, 6-7, and 8-9. Using commonly available sources, such as signal generators or defibrillators, to drive the electrodes, the required switching from one set of electrodes (odd-even) to another set of electrodes (even-odd) is done either manually or using slow switches.

The exemplary embodiments of the present invention that are described herein address the requirements for switching between sets of electrodes by providing a medical apparatus comprising a versatile electrical signal generator for IRE, with capabilities of fast switching and generation of a variety of therapeutic signals. The signal generator operates in conjunction with a probe, comprising a catheter with multiple electrodes arrayed along the catheter, which is inserted into the body of the patient so that the electrodes contact tissue within the body.

Each electrode along the catheter (except the first and last electrodes in the array) has neighboring electrodes on both sides. In some exemplary embodiments, during a first period of time, the signal generator applies IRE pulses between each electrode and a first of its two neighbors, for example between pairs 1-2, 3-4, . . . 9-10. Then, during a second period of time it applies the IRE pulses between each electrode and its second neighbor, for example, pairs 2-3, 4-5, . . . 8-9. In other words, by defining the labels "first neighbor" and "second neighbor" appropriately, the above application of IRE pulses energizes the odd-even electrodes during the first period of time and the even-odd electrodes during the second period of time.

In the disclosed exemplary embodiments, the signal generator, configured as an IRE generator, comprises a network of fast switches, enabling switching between the odd-even and even-odd electrodes in a matter of milliseconds or less. By incorporating additional relays in the network, it may be configured for applying the IRE pulses to other configurations of electrodes, such as, for example, interleaved electrodes, with a concomitant fast switching between sets of interleaved electrodes.

As noted earlier, the two commonly used methods of ablation, IRE ablation and RF ablation, implement different modalities: IRE ablation destroys cells by punching holes in the cell membranes, whereas RF ablation destroys the cells by heating. It can be advantageous to combine these two methods in treating the same tissue.

Thus, in some exemplary embodiments of the present invention that are described herein, the electrical signal generator is capable of switching rapidly between the two modalities of IRE ablation and RF ablation. The electrical signal generator thus applies an alternating sequence of IRE pulses and a RF signal between one or more pairs of the electrodes.

In the disclosed exemplary embodiments, the signal generator, configured as an IRE generator, functions in two rapidly switchable modalities: In an IRE modality, it generates IRE pulses for IRE ablation; in an RF modality, the signal generator generates a pulse train at a frequency suitable for RF ablation and with a lower amplitude than IRE pulses. This pulse train is converted to a sinusoidal RF ablation signal by filtering it through a low-pass filter. Rapid switching between these two modalities, while coupling both the IRE and the RF ablation signals to the same electrodes, is accomplished by alternatingly closing and opening a bypass switch in parallel with the low-pass filter. The RF ablation signal may be inserted either between two consecutive bipolar IRE pulses or between the positive and negative pulses of a single bipolar IRE pulse. In the latter case, the spacing between the positive and negative pulse is stretched to 1-10 ms.

The IRE generator is controlled by an IRE controller implementing an ablation protocol. The protocol defines the values for all of the parameters of the IRE ablation, including an additionally incorporated RF ablation in some cases, to suit the targeted tissue and the electrode configuration of the catheter. These parameter values are set at the start of the IRE procedure by a medical professional, such as a physician, controlling the procedure. The physician sets the parameters based on the required tissue volume, field strength, catheter configuration, and the energy per pulse or pulse train, as well as the energy to be delivered over the entire procedure.

Ire Ablation System and Ire Pulses

FIG. 1 is a schematic pictorial illustration of a multi-channel IRE system 20 used in an IRE ablation procedure, in accordance with exemplary embodiments of the present invention. In the following description, the IRE ablation procedure will also be referred to as "IRE ablation" or "IRE procedure." In the illustrated exemplary embodiment, a physician 22 is performing a multi-channel IRE ablation procedure using IRE system 20. Physician 22 is performing the procedure on a subject 24, using an ablation catheter 26 whose distal end 28 comprises multiple ablation electrodes 30 arrayed along the length of the catheter.

IRE system 20 comprises a processor 32 and an IRE module 34, wherein the IRE module comprises an IRE generator 36 and an IRE controller 38. As will be further detailed below, IRE generator 36 generates trains of electrical pulses, which are directed to selected electrodes 30 for performing an IRE procedure. The waveforms (timing and amplitude) of the trains of electrical pulses are controlled by IRE controller 38. Processor 32, as will also be detailed below, handles the input and output interface between IRE system 20 and physician 22.

Processor 32 and IRE controller 38 each typically comprises a programmable processor, which is programmed in software and/or firmware to carry out the functions that are described herein. Alternatively or additionally, each of them may comprise hard-wired and/or programmable hardware logic circuits, which carry out at least some of these functions. Although processor 32 and IRE controller 38 are shown in the figures, for the sake of simplicity, as separate, monolithic functional blocks, in practice some of these functions may be combined in a single processing and control unit, with suitable interfaces for receiving and outputting the signals that are illustrated in the figures and are described in the text. In some exemplary embodiments, IRE controller 38 resides within IRE module 34, as high-speed control signals are transmitted from the IRE controller to IRE generator 36. However, provided that signals at sufficiently high speeds may be transmitted from processor 32 to IRE generator 36, IRE controller 38 may reside within the processor.

Processor 32 and IRE module 34 typically reside within a console 40. Console 40 comprises input devices 42, such as a keyboard and a mouse. A display screen 44 is located in proximity to (or integral to) console 40. Display screen 44 may optionally comprise a touch screen, thus providing another input device.

IRE system 20 may additionally comprise one or more of the following modules (typically residing within console 40), connected to suitable interfaces and devices in system 20:

An electrocardiogram (ECG) module 46 is coupled through a cable 48 to ECG electrodes 50, which are attached to subject 24. ECG module 46 is configured to measure the electrical activity of a heart 52 of subject 24.

A temperature module 54 is coupled to optional temperature sensors, such as thermocouples 56 located adjacent to each electrode 30 on distal end 28 of catheter 26, and is configured to measure the temperature of adjacent tissue 58.

A tracking module 60 is coupled to one or more electromagnetic position sensors (not shown) in distal end 28. In the presence of an external magnetic field generated by one or more magnetic-field generators 62, the electromagnetic position sensors output signals that vary with the positions of the sensors. Based on these signals, tracking module 60 may ascertain the positions of electrodes 30 in heart 52.

The above modules 46, 54, and 60 typically comprise both analog and digital components, and are configured to receive analog signals and transmit digital signals. Each module may additionally comprise hard-wired and/or programmable hardware logic circuits, which carry out at least some of the functions of the module.

Catheter 26 is coupled to console 40 via an electrical interface 64, such as a port or socket. IRE signals are thus carried to distal end 28 via interface 64. Similarly, signals for tracking the position of distal end 28, and/or signals for tracking the temperature of tissue 58, may be received by processor 32 via interface 64 and applied by IRE controller 38 in controlling the pulses generated by IRE generator 36.

An external electrode 65, or "return patch", may be additionally coupled externally between subject 24, typically on the skin of the subject's torso, and IRE generator 36.

Processor 32 receives from physician 22 (or from other user), prior to and/or during the IRE procedure, setup parameters 66 for the procedure. Using one or more suitable input devices 42, physician 22 sets the parameters of the IRE pulse train, as explained below with reference to FIGS. 2-4 and Table 1. Physician 22 further selects pairs of ablation electrodes 30 for activation (for receiving the IRE pulse trains) and the order in which they are activated.

In setting up the IRE ablation, physician 22 may also choose the mode of synchronization of the burst of IRE pulses with respect to the cycle of heart 52. A first option, which is called a "synchronous mode," is to synchronize the IRE pulse burst to take place during the refractory state of heart 52, when the heart is recharging and will not respond to external electrical pulses. The burst is timed to take place after the QRS-complex of heart 52, wherein the delay is approximately 50% of the cycle time of the heart, so that the burst takes place during the T-wave of heart 52, before the P-wave. In order to implement synchronous mode, IRE controller 38 times the burst or bursts of IRE pulses based on ECG signals 414 from ECG module 46, shown in FIG. 5, below.

A second synchronization option is an asynchronous mode, wherein the burst of IRE pulses is launched independently of the timing of heart 52. This option is possible, since the IRE burst, typically of a length of 200 ms, with a maximal length of 500 ms, is felt by the heart as one short pulse, to which the heart does not react. Asynchronous operation of this sort can be useful in simplifying and streamlining the IRE procedure.

In response to receiving setup parameters 66, processor 32 communicates these parameters to IRE controller 38, which commands IRE generator 36 to generate IRE signals in accordance with the setup requested by physician 22. Additionally, processor 32 may display setup parameters 66 on display screen 44.

In some exemplary embodiments, processor 32 displays on display 44, based on signals received from tracking module 60, a relevant image 68 of the subject's anatomy, annotated, for example, to show the current position and orientation of distal end 28. Alternatively or additionally, based on signals received from temperature module 54 and ECG module 46, processor 32 may display on display screen 44 the temperatures of tissue 58 at each electrode 30 and the electrical activity of heart 52.

To begin the procedure, physician 22 inserts catheter 26 into subject 24, and then navigates the catheter, using a control handle 70, to an appropriate site within, or external to, heart 52. Subsequently, physician 22 brings distal end 28 into contact with tissue 58, such as myocardial or epicardial tissue, of heart 52. Next, IRE generator 36 generates multiple IRE signals, as explained below with reference to FIG. 3. The IRE signals are carried through catheter 26, over different respective channels, to pairs of ablation electrodes 30, such that currents 72 generated by the IRE pulses flow between the electrodes of each pair (bipolar ablation), and perform the requested irreversible electroporation on tissue 58.

FIG. 2 is a schematic illustration of a bipolar IRE pulse 100, in accordance with an exemplary embodiment of the present invention.

A curve 102 depicts the voltage V of bipolar IRE pulse 100 as a function of time t in an IRE ablation procedure. The bipolar IRE pulse comprises a positive pulse 104 and a negative pulse 106, wherein the terms "positive" and "negative" refer to an arbitrarily chosen polarity of the two electrodes 30 between which the bipolar pulse is applied. The amplitude of positive pulse 104 is labeled as V+, and the temporal width of the pulse is labeled as t+. Similarly, the amplitude of negative pulse 106 is labeled as V−, and the temporal width of the pulse is labeled as t−. The temporal width between positive pulse 104 and negative pulse 106 is labeled as $t_{SPACE}$. Typical values for the parameters of bipolar pulse 100 are given in Table 1, below.

FIG. 3 is a schematic illustration of a burst 200 of bipolar pulses, in accordance with an exemplary embodiment of the present invention.

In an IRE procedure, the IRE signals are delivered to electrodes 30 as one or more bursts 200, depicted by a curve 202. Burst 200 comprises $N_T$ pulse trains 204, wherein each train comprises $N_P$ bipolar pulses 100. The length of pulse train 204 is labeled as $t_T$. The period of bipolar pulses 100 within a pulse train 204 is labeled as $t_{PP}$, and the interval between consecutive trains is labeled as $\Delta_T$, during which the signals are not applied. Typical values for the parameters of burst 200 are given in Table 1, below.

Figure 4B:
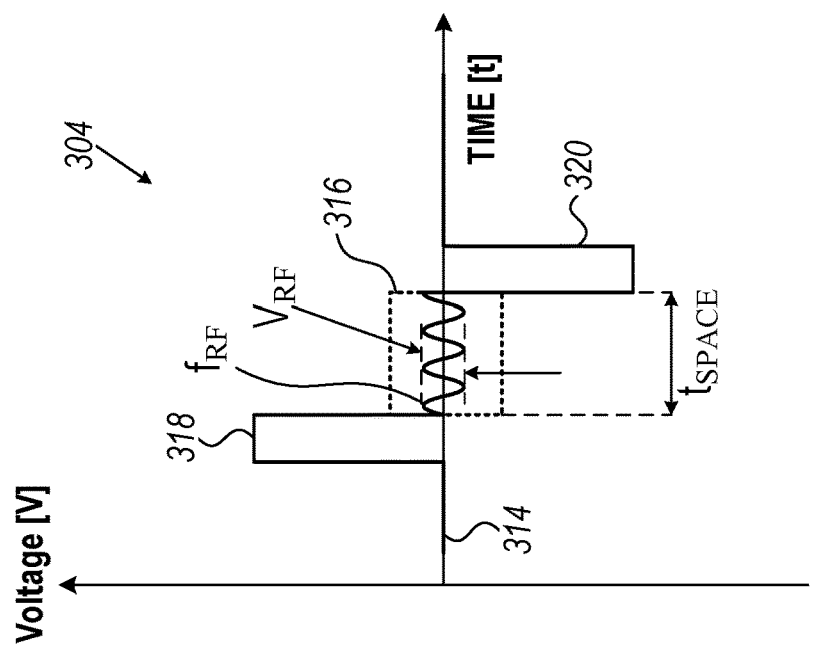
FIGS. 4A-B are schematic illustrations of IRE signals with an incorporated RF signal, in accordance with an exemplary embodiment of the present invention.
Figure 4A:
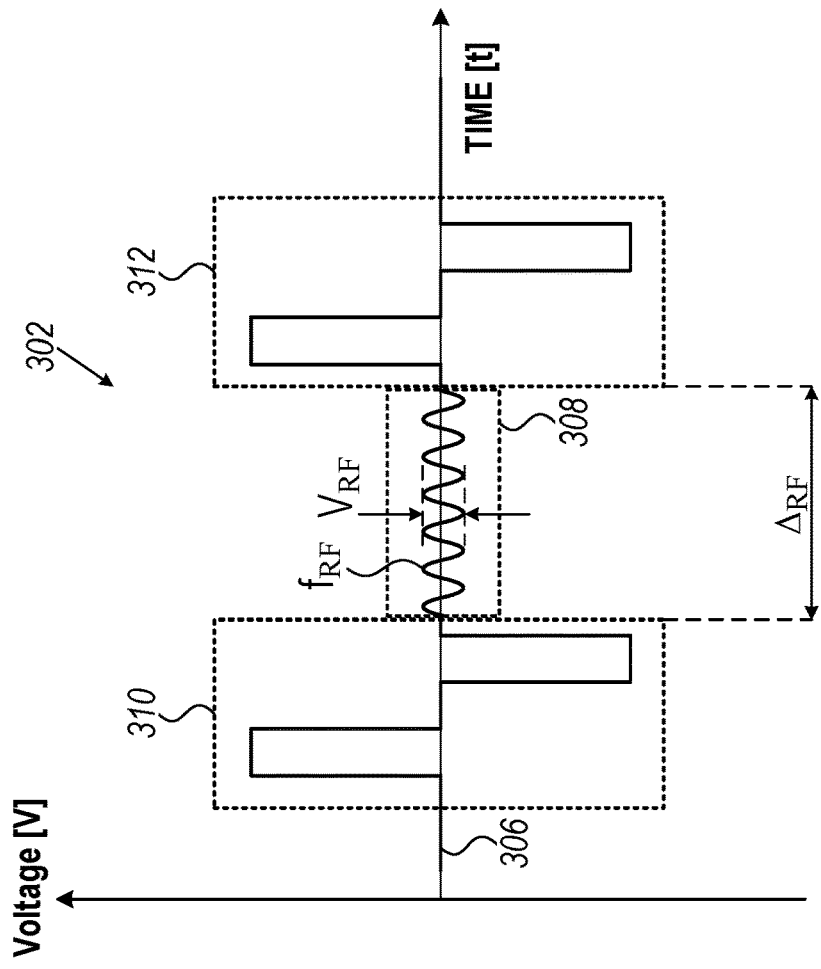

FIGS. 4A-B are schematic illustrations of IRE signals 302 and 304 with an incorporated RF signal, in accordance with exemplary embodiments of the present invention. In the exemplary embodiments shown in FIGS. 4A-B, RF ablation is combined with IRE ablation in order to benefit from both of these ablation modalities.

In FIG. 4A, a curve 306 depicts the voltage V as a function of time t of an RF signal 308 between two bipolar pulses 310 and 312, similar to bipolar pulse 100 of FIG. 2. The amplitude of RF signal 308 is labeled as $V_{RF}$ and its frequency is labeled as $f_{RF}$, and the separation between bipolar pulses 310 and 312 is labeled as $\Delta_{RF}$. Typically the frequency $f_{RF}$ is between 350 and 500 kHz, and the amplitude $V_{RF}$ is between 10 and 200 V, but higher or lower frequencies and amplitudes may alternatively be used.

In FIG. 4B, a curve 314 depicts the voltage V as a function of time t of an RF signal 316 between a positive IRE pulse 318 and a negative IRE pulse 320. IRE pulses 318 and 320 are similar to pulses 104 and 106 of FIG. 2. In this exemplary embodiment, the spacing $t_{SPACE}$ between positive and negative pulses 318 and 320 has been stretched, as indicated in Table 1.

Typical values of the amplitude and frequency of RF signals 308 and 316 are given in Table 1. When an RF signal is inserted into the IRE signal, as depicted either in FIG. 4A or FIG. 4B, the combination of the two signals is repeated to the end of the ablation procedure.

TABLE 1

Typical values for the parameters of IRE signals

| Parameter | Symbol | Typical values |
|---|---|---|
| Pulse amplitudes | V+, V− | 500-2000 V |
| Pulse widths | t+, t− | 0.5-5 μs |
| Spacing between positive and negative pulse | $t_{SPACE}$ | 0.1-5 μs (1-10 ms when an optional RF signal is inserted between the positive and negative pulses) |
| Period of bipolar pulses in a pulse train | $t_{PP}$ | 1-20 μs |
| Length of pulse train | $t_T$ | 100 μs |
| Number of bipolar pulses in a pulse train | $N_P$ | 1-100 |
| Spacing between consecutive pulse trains | $\Delta_T$ | 0.3-1000 ms |
| Number of pulse trains in a burst | $N_T$ | 1-100 |
| Length of a burst | | 0-500 ms |
| Energy per channel | | ≤60 J |
| Total time for IRE signal delivery | | ≤10 s |
| Amplitude of optional RF signal | $V_{RF}$ | 10-200 V |
| Frequency of optional RF signal | $f_{RF}$ | 500 kHz |

Ire Module

Figure 5:
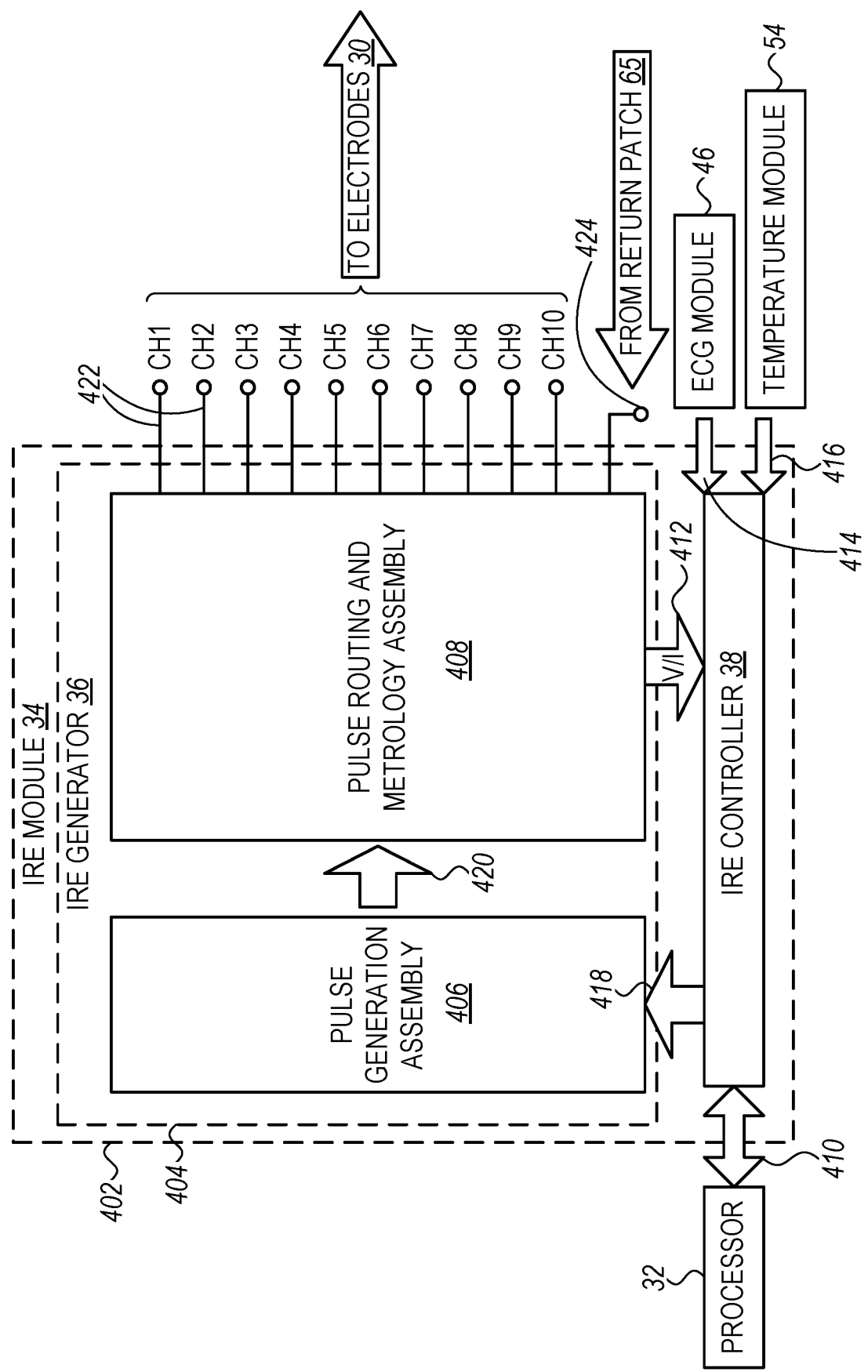
FIG. 5 is a block diagram that schematically illustrates an IRE module and its connections to other modules, in accordance with an exemplary embodiment of the present invention.

FIG. 5 is a block diagram that schematically shows details of IRE module 34 and its connections to other modules in system 20, in accordance with an exemplary embodiment of the present invention.

With reference to FIG. 1, IRE module 34 comprises IRE generator 36 and IRE controller 38. IRE module 34 is delineated in FIG. 5 by an outer dotted-line frame 402. Within frame 402, IRE generator 36 is delineated by an inner dotted-line frame 404. IRE generator 36 comprises a pulse generation assembly 406 and a pulse routing and metrology assembly 408, which will both be further detailed in FIGS. 6-9, below.

IRE controller 38 communicates with processor 32 through bi-directional signals 410, wherein the processor communicates to the IRE controller commands reflecting setup parameters 66. IRE controller 38 further receives digital voltage and current signals 412 from pulse routing and metrology assembly 408, digital ECG signals 414 from ECG module 46, and digital temperature signals 416 from temperature module 54, and communicates these signals through bi-directional signals 410 to processor 32.

IRE controller 38 communicates to pulse generation assembly 406 digital command signals 418, derived from setup parameters 66, commanding IRE generator 36 to generate IRE pulses, such as those shown in FIGS. 3-5, above. These IRE pulses are sent to pulse routing and metrology assembly 408 as analog pulse signals 420. Pulse routing and metrology assembly 408 is coupled to electrodes 30 through output channels 422, as well as to return patch 65 through connection 424. FIG. 5 shows ten output channels 422, labelled CH1-CH10. In the following description, a specific electrode is called by the name of the specific channel coupled to it; for example, electrode CH5 relates to the electrode that is coupled to CH5 of channels 422. Although FIG. 5 refers to ten channels 422, IRE generator may alternatively comprise a different number of channels, for example 8, 16, or 20 channels, or any other suitable number of channels.

Figure 6:
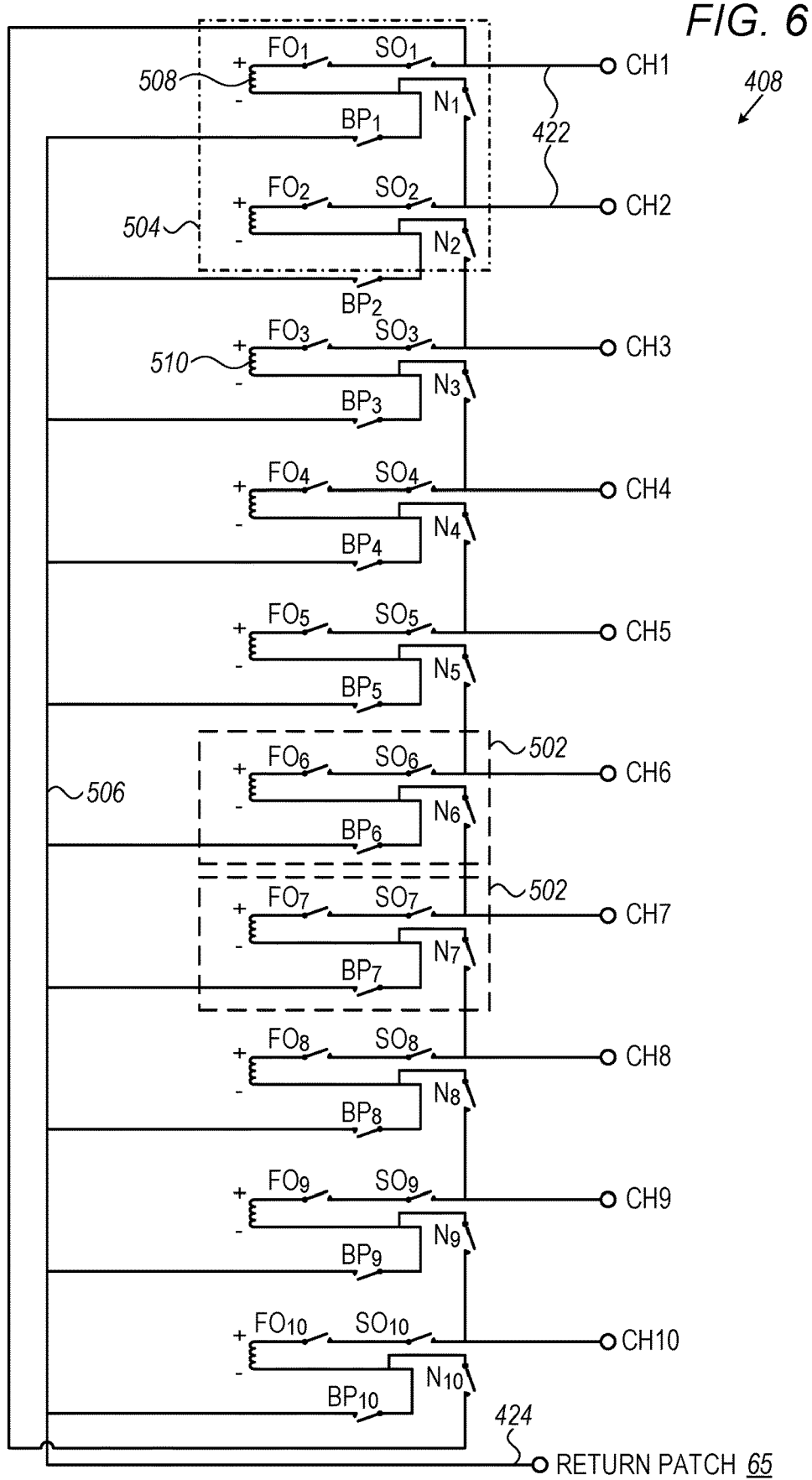
FIG. 6 is an electrical schematic diagram of a pulse routing and metrology assembly in the IRE module of FIG. 5.

FIG. 6 is an electrical schematic diagram of pulse routing and metrology assembly 408 of FIG. 5, in accordance with an exemplary embodiment of the present invention. For the sake of clarity, the circuits involved in measuring currents and voltages, have been omitted. These circuits will be detailed in FIG. 7, below. Output channels 422 and connection 424 are shown in FIG. 6 using the same labels as in FIG. 5.

Pulse routing and metrology assembly 408 comprises modules 502, with one module for each output channel 422. A pair 504 of adjacent modules 502 is shown in detail in FIG. 7, below.

Each module 502 comprises switches, labelled as $FO_i$, $SO_i$, $N_i$, and $BP_i$ for the $i^{th}$ module. Switches $FO_i$ are all fast switches for switching the IRE ablation from channel to channel, whereas switches $SO_i$, $N_i$, and $BP_i$ are slower relays, used to set up pulse routing and metrology assembly 408 for a given mode of IRE ablation. A typical switching time for fast switches $FO_i$ is shorter than 0.3 μs, whereas slow relays $SO_i$, $N_i$, and $BP_i$ require a switching time of only 3 ms. The examples that are given below demonstrate uses of the switches and relays.

Example 1 demonstrates the use of the switches and relays for IRE ablation between pairs of electrodes according to an odd-even scheme CH1-CH2, CH3-CH4, CH5-CH6, CH7-CH8, and CH9-CH10. (Here the bipolar pulses are applied between each electrode and a first neighbor.) The settings of the switches and relays are shown in Table 2, below.

TABLE 2

Switch and relay settings for Example 1

| Channel $CH_i$ | Fast switch $FO_i$ | Slow relay $SO_i$ | Slow relay $N_i$ | Slow relay $BP_i$ |
|---|---|---|---|---|
| CH1 | ON | ON | ON | OFF |
| CH2 | OFF | ON | ON | OFF |
| CH3 | ON | ON | ON | OFF |
| CH4 | OFF | ON | ON | OFF |
| CH5 | ON | ON | ON | OFF |
| CH6 | OFF | ON | ON | OFF |
| CH7 | ON | ON | ON | OFF |
| CH8 | OFF | ON | ON | OFF |
| CH9 | ON | ON | ON | OFF |
| CH10 | OFF | ON | ON | OFF |

Example 2 demonstrates the use of the switches and relays for IRE ablation between pairs of electrodes according to an even-odd scheme CH2-CH3, CH4-CH5, CH6-CH7, and CH8-CH9 (in which the bipolar pulses are applied between each electrode and its second neighbor). For a circular catheter 26, wherein the first and last of electrodes lie side-by-side, the pair CH10-CH1 may be added to the even-odd pairs. The settings of the switches and relays are shown in Table 3, below.

TABLE 3

Switch and relay settings for Example 2

| Channel $CH_i$ | Fast switch $FO_i$ | Slow relay $SO_i$ | Slow relay $N_i$ | Slow relay $BP_i$ |
|---|---|---|---|---|
| CH1 | OFF | ON | ON | OFF |
| CH2 | ON | ON | ON | OFF |
| CH3 | OFF | ON | ON | OFF |
| CH4 | ON | ON | ON | OFF |
| CH5 | OFF | ON | ON | OFF |
| CH6 | ON | ON | ON | OFF |
| CH7 | OFF | ON | ON | OFF |
| CH8 | ON | ON | ON | OFF |
| CH9 | OFF | ON | ON | OFF |
| CH10 | ON | ON | ON | OFF |

Combining Examples 1 and 2, a fast IRE ablation between all pairs of electrodes 30 may be accomplished by first ablating with the even-odd scheme of Example 1, then switching each fast switch $FO_i$ to an opposite state (from ON to OFF and from OFF to ON), and then ablating with the odd-even scheme of Example 2. As slow relays $SO_i$, $N_i$, and $BP_i$ are not required to switch their states, the switching takes place at the speed of the $FO_i$ switches.

Example 3 demonstrates IRE ablation between non-adjacent electrodes 30, in this example CH1-CH3, CH4-CH6, and CH7-CH9. Such a configuration may be utilized to cause deeper lesions in tissue 58. The settings of the switches and relays are shown in Table 4, below.

TABLE 4

Switch and relay settings for Example 3

| Channel $CH_i$ | Fast switch $FO_i$ | Slow relay $SO_i$ | Slow relay $N_i$ | Slow relay $BP_i$ |
|---|---|---|---|---|
| CH1 | ON | ON | ON | OFF |
| CH2 | ON | ON | ON | OFF |
| CH3 | OFF | ON | ON | OFF |
| CH4 | ON | ON | ON | OFF |
| CH5 | ON | ON | ON | OFF |
| CH6 | OFF | ON | ON | OFF |
| CH7 | ON | ON | ON | OFF |
| CH8 | ON | ON | ON | OFF |
| CH9 | OFF | ON | ON | OFF |
| CH10 | OFF | ON | ON | OFF |

Again, other pairs of electrodes may be rapidly chosen by reconfiguring switches $FO_i$.

Example 4 demonstrates an alternative way to perform an ablation between channels CH1 and CH3. In this example, a BP line 506 is utilized to close the ablation circuit. The settings of the switches and relays are shown in Table 5, below.

TABLE 5

Switch and relay settings for Example 4

| Channel $CH_i$ | Fast switch $FO_i$ | Slow relay $SO_i$ | Slow relay $N_i$ | Slow relay $BP_i$ |
|---|---|---|---|---|
| CH1 | ON | ON | OFF | ON |
| CH2 | OFF | ON | OFF | OFF |
| CH3 | ON | ON | OFF | ON |
| CH4 | OFF | ON | OFF | OFF |
| CH5 | ON | ON | OFF | OFF |
| CH6 | OFF | ON | OFF | OFF |
| CH7 | ON | ON | OFF | OFF |
| CH8 | OFF | ON | OFF | OFF |

TABLE 5-continued

Switch and relay settings for Example 4

| Channel $CH_i$ | Fast switch $FO_i$ | Slow relay $SO_i$ | Slow relay $N_i$ | Slow relay $BP_i$ |
|---|---|---|---|---|
| CH9 | ON | ON | OFF | OFF |
| CH10 | OFF | ON | OFF | OFF |

In Example 4, the electrical path in pulse routing and metrology assembly 408 couples transformer secondaries 508 and 510 in series. As the distance between electrodes CH1 and CH3 is double to that between adjacent electrodes (for example CH1 and CH2), the voltage between CH1 and CH3 has to be double the voltage between adjacent electrodes so as to have the same electrical field strength between the respective electrodes. This is accomplished by driving the primaries for these two secondaries in opposite phases. Slow switches $SO_i$ are all left in the ON-state in preparation for the next ablation between another pair of electrodes, for example between CH2 and CH4.

As shown in the above examples, the implementation of pulse routing and metrology assembly 408 using relays and fast switches enables a flexible and fast distribution of IRE pulses to electrodes 30, as well as a flexible re-configuration of the applied IRE pulse amplitudes.

Figure 7:
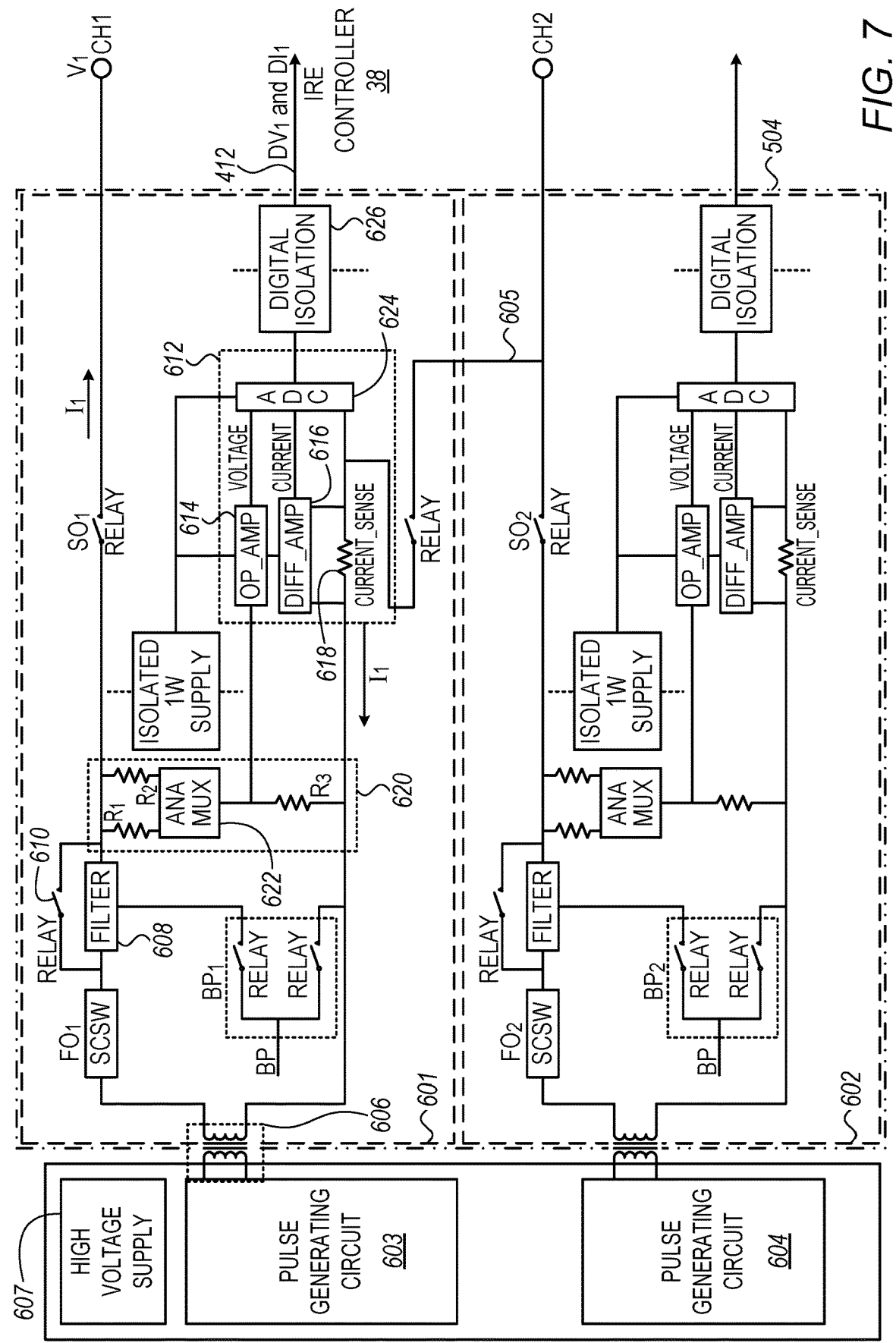
FIG. 7 is an electrical schematic diagram of two adjacent modules in the pulse routing and metrology assembly of FIG. 6.

FIG. 7 is an electrical schematic diagram of two adjacent modules 601 and 602 of pulse routing and metrology assembly 408, in accordance with an exemplary embodiment of the present invention.

Modules 601 and 602 make up pair 504 of FIG. 6, as is shown by dash-dot frame with the same label (504). Modules 601 and 602 are fed by pulse generating circuits 603 and 604, respectively, which comprise, with reference to FIG. 5, parts of pulse generation assembly 406. Modules 601 and 602, in turn, feed channels CH1 and CH2, respectively, similarly to modules 502 of pair 504 in FIG. 6. Two modules 601 and 602 are shown in FIG. 7 in order to show a connection 605 between the modules. As the two modules are identical (and identical to the additional modules in pulse routing and metrology assembly 408), only module 601 is described in detail below.

Figure 8:
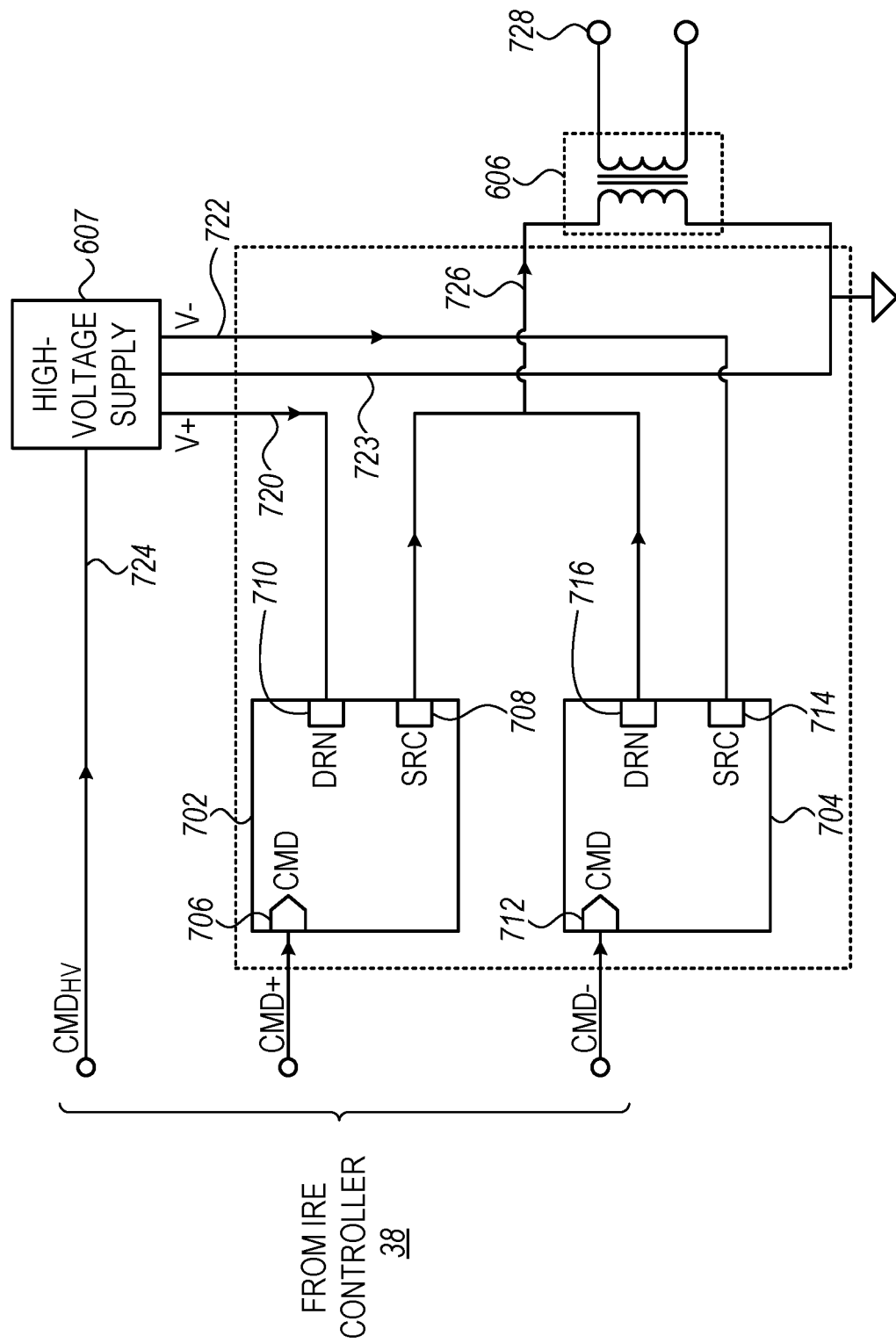
FIG. 8 is an electrical schematic diagram of a pulse generating circuit, a transformer, and a high-voltage supply, in accordance with an exemplary embodiment of the present invention.
Figure 9:
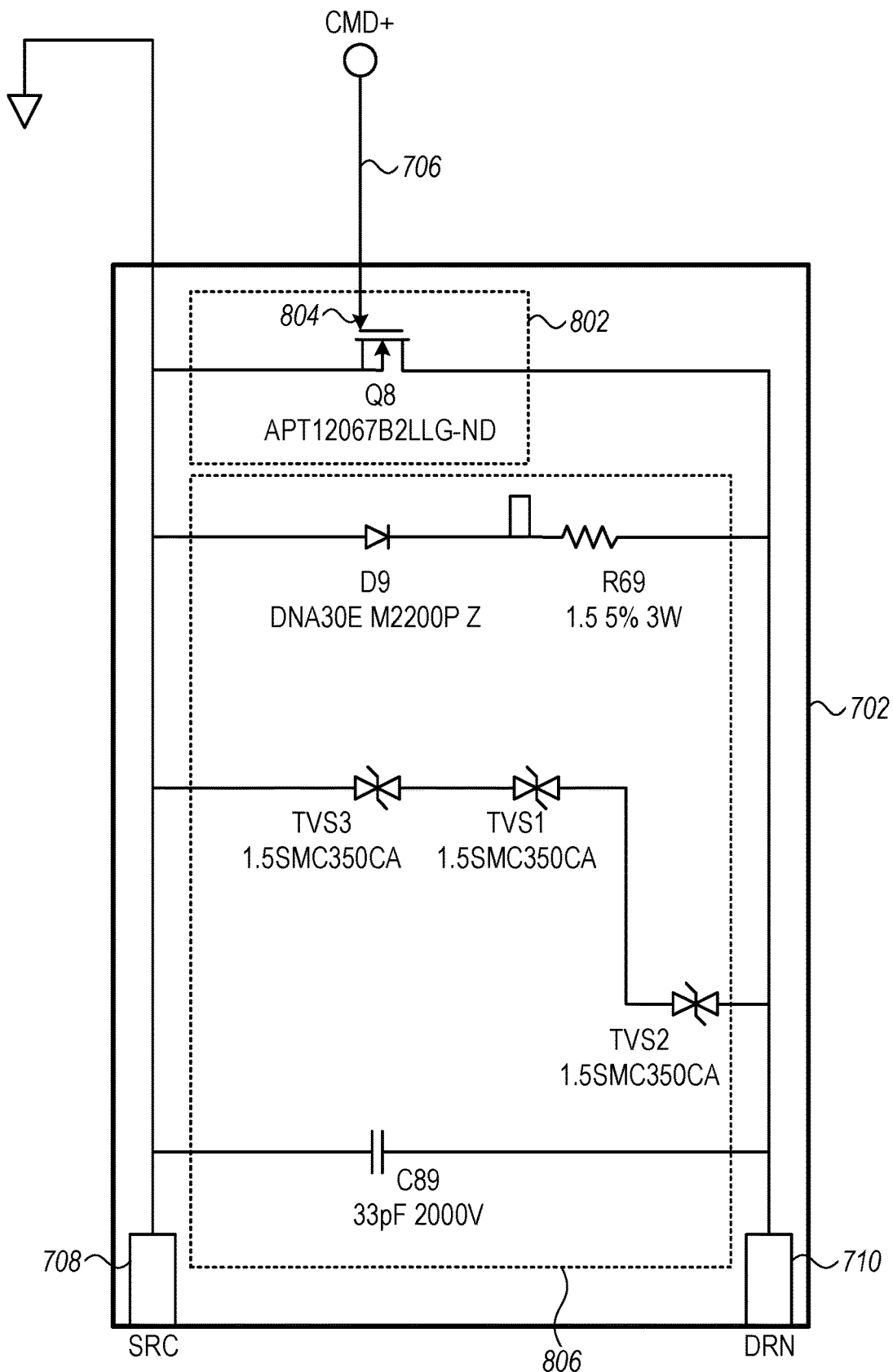
FIG. 9 is an electrical schematic diagram of a switch, in accordance with an exemplary embodiment of the present invention.

Further details of pulse generating circuits 603 and 604 are shown in FIGS. 8-9, below. Pulse generation assembly 406 comprises one pulse generating circuit similar to circuits 603 and 604 for each channel of IRE generator 36. Pulse generation assembly 406 further comprises a high-voltage supply 607, detailed in FIG. 8.

Pulse generating circuit 603 is coupled to module 601 by a transformer 606. Fast switch $FO_1$ and slow relays $SO_1$, $N_1$, and $BP_1$ are labelled similarly to FIG. 6. A low-pass filter 608 converts a pulse train transmitted by pulse generating circuit 603 via transformer 606 and switch $FO_1$ to a sinusoidal signal, allowing CH1 to be used for RF ablation. (Similarly, each channel of IRE generator 36 may be independently used for RF ablation.) The engagement of filter 608 is controlled by a relay 610. An RF signal having a given frequency $f_{RF}$ and amplitude $V_{RF}$ is produced by pulse generating circuit 603 emitting a train of bipolar pulses at the frequency $f_{RF}$ through low-pass filter 608, which converts this pulse train to a sinusoidal signal with the frequency $f_{RF}$. The amplitude of the train of bipolar pulses is adjusted so that the amplitude of the sinusoidal signal is $V_{RF}$.

A voltage $V_1$ and current $I_1$ coupled to CH1 are shown in FIG. 7 as a voltage between channels CH1 and CH2, and a current flowing to CH1 and returning from CH2.

$V_1$ and $I_1$ are measured by a metrology module 612, comprising an operational amplifier 614 for measuring the voltage and a differential amplifier 616 measuring the current across a current sense resistor 618. Voltage $V_1$ is measured from a voltage divider 620, comprising resistors $R_1$, $R_2$, and $R_3$, and an analog multiplexer 622. Analog multiplexer 622 couples in either resistor $R_1$ or $R_2$, so that the voltage dividing ratio of voltage divider 620 is either $R_1/R_3$ or $R_2/R_3$. Metrology module 612 further comprises an analog-to-digital converter (ADC) 624 for converting the measured analog voltage $V_1$ and current $I_1$ to digital signals $DV_1$ and $DI_1$. These digital signals are sent through a digital isolator 626 to IRE controller 38 as signals 412 (FIG. 5). Digital isolator 626 protects subject 24 (FIG. 1) from unwanted electrical voltages and currents.

Switch $FO_1$, relays $SO_1$, $BP_1$, $N_1$ and 610, and analog multiplexer 622 are driven by IRE controller 38. For the sake of simplicity, the respective control lines are not shown in FIG. 7.

FIG. 8 is an electrical schematic diagram of pulse generating circuit 603, transformer 606, and high-voltage supply 607, in accordance with an exemplary embodiment of the present invention.

Pulse generating circuit 603 (FIG. 7) comprises two switches 702 and 704, whose internal details are further shown in FIG. 9, below. Switch 702 comprises a command input 706, a source 708, and a drain 710. Switch 704 comprises a command input 712, a source 714, and a drain 716. Together switches 702 and 704 form a half of an H-bridge (as is known in the art), also called a "half bridge."

High-voltage supply 607 supplies to respective outputs 720 and 722 a positive voltage V+ and a negative voltage V−, adjustable within respective positive and negative ranges of ±(10-2000) V responsively to a signal received by a high-voltage command input 724 from IRE controller 38. High-voltage supply 607 also provides a ground connection 723. A single high-voltage supply 607 is coupled to all pulse generating circuits of pulse generation assembly 406. Alternatively, each pulse generating circuit may be coupled to a separate high-voltage supply.

Drain 710 of switch 702 is coupled to positive voltage output 720, and source 708 of the switch is coupled to an input 726 of transformer 606. When command input 706 receives a command signal CMD+, positive voltage V+ is coupled from positive voltage output 720 to transformer input 726 via switch 702. Source 714 of switch 704 is coupled to negative voltage output 722, and drain 716 of the switch is coupled to transformer input 726. When command input 712 receives a command signal CMD−, negative voltage V− is coupled from negative voltage output 722 to transformer input 726 via switch 704. Thus, by alternately activating the two command signals CMD+ and CMD−, positive and negative pulses, respectively, are coupled to transformer input 726, and then transmitted by transformer 606 to its output 728. The timing of the pulses (their widths and separation) are controlled by command signals CMD+ and CMD−, and the amplitudes of the pulses are controlled by a high-voltage command signal $CMD_{HV}$ to high-voltage command input 724. All three command signals CMD+, CMD−, and $CMD_{HV}$ are received from IRE controller 38, which thus controls the pulses fed into the respective channel of pulse routing and metrology assembly 408.

In an alternative exemplary embodiment (not shown in the figures), a full H-bridge is utilized, with a single-polarity high-voltage supply. This configuration may also be used to produce both positive and negative pulses from the single-polarity source, in response to signals controlling the full H-bridge. An advantage of this embodiment is that it can use a simpler high-voltage supply, whereas the advantage of a half bridge and a dual high-voltage power supply is that it provides a fixed ground potential, as well as independently adjustable positive and negative voltages.

FIG. 9 is an electrical schematic diagram of switch 702, in accordance with an exemplary embodiment of the present invention. Switch 704 is implemented in a similar fashion to switch 702.

The switching function of switch 702 is implemented by a field-effect transistor (FET) 802, comprising a gate 804, source 708, and drain 710. Command input 706 is coupled to gate 804, with source 708 and drain 710 coupled as shown in FIG. 8. Additional components 806, comprising Zener diodes, a diode, a resistor, and a capacitor, function as circuit protectors.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus for tissue ablation, comprising:
   a probe having a distal end, a proximal end and a length configured for insertion into a body of a patient and comprising an array of electrodes disposed successively along the length of the probe configured to contact tissue within the body, the array of electrodes having a proximal electrode at the proximal end of the probe and a distal electrode at distal end of the probe and a plurality of intermediary electrodes between the proximal and distal electrodes; and
   an electrical signal generator configured to apply between one or more pairs of the array of electrodes, signals of first and second types in alternation, the signals of the first type comprising a plurality of sequences of bipolar pulses, each sequence of the bipolar pulses having a duration and an amplitude sufficient to cause irreversible electroporation (IRE) in the tissue contacted by the array of electrodes, a first sequence of bipolar pulses of the plurality of sequences of bipolar pulses being applied to odd-even pairs of electrodes for all of the array of electrodes during a first period of time, the odd-even pairs of electrodes beginning with a pair comprising the proximal electrode and an electrode of the plurality of intermediary electrodes immediately adjacent the proximal electrode and continuing successively for each remaining pair of the electrodes in the array, and a second sequence of bipolar pulses of the plurality of sequences of bipolar pulses being applied to even-odd pairs of electrodes of the array of electrodes during a second period of time, the even-odd pairs of electrodes beginning with a pair comprising the electrode immediately adjacent the proximal electrode and a successive immediately adjacent electrode of the plurality of intermediary electrodes and continuing successively for each remaining pair of the of electrodes in the array, and the signals of the second type comprising a radio-frequency (RF) signal having a power sufficient to thermally ablate the tissue contacted by the electrodes.

2. The medical apparatus according to claim 1, wherein the electrical signal generator is further configured to apply the signals of the first type without the alternation with the signals of the second type.

3. The medical apparatus according to claim 1, wherein the electrical signal generator is further configured to apply the signals of the second type without the alternation with the signals of the first type.

4. The medical apparatus according to claim 1, wherein each of the plurality of sequences of bipolar pulses comprises pulses, the amplitude being at least 200 V, and the duration of each of the bipolar pulses being less than 20 µs.

5. The medical apparatus according to claim 1, wherein the RF signal has a frequency between 350 and 500 kHz and an amplitude between 10 and 200 V.

6. The medical apparatus according to claim 1, and comprising a controller configured to transmit control signals to the electrical signal generator, and wherein the electrical signal generator comprises:
a pulse generation assembly, configured to receive the control signals from the controller and to transmit the plurality of sequences of bipolar pulses responsive to the control signals; and
a pulse routing and metrology assembly, comprising a configurable network of multiple, mutually connected fast switches and slow relays, which are configured to receive the control signals from the controller, to receive the plurality of sequences of bipolar pulses from the pulse generation assembly, and to transmit the plurality of sequences of bipolar pulses to the plurality of electrodes responsively to the received control signals.

7. The medical apparatus according to claim 6, wherein the electrical signal generator comprises a low-pass filter, which is configured to receive and filter a pulse train from the pulse generation assembly so as to convert the pulse train to the RF signal, thereby generating the signals of the second type.

8. The medical apparatus according to claim 1, wherein each of the plurality of sequences of bipolar pulses of the signals of the first type comprises a positive pulse and a negative pulse, and wherein the signals of the second type are interleaved between the positive and negative pulses of each of the plurality of sequences of bipolar pulses of the signals of the first type.

9. The medical apparatus according to claim 1, wherein each of the plurality of sequences of bipolar pulses of the signals of the first type comprises a positive pulse and a negative pulse, and wherein the signals of the second type are interleaved between successive sequences of the plurality of sequences of bipolar pulses.

10. The medical apparatus according to claim 1, wherein the electrical signal generator is configured to generate a plurality of pulse trains, each pulse train comprising the signals of the first and second types, wherein the pulse trains are separated by intervals in which the signals are not applied.

11. The medical apparatus according to claim 1, wherein the probe comprises a plurality of temperature sensors adjacent to the plurality of electrodes, and wherein the electrical signal generator is configured to apply the signals responsively to a temperature measured by the temperature sensors.

12. The medical apparatus according to claim 1, wherein the probe is configured to contact the tissue in a heart of the patient and to apply the signals so as to ablate the tissue in the heart.

13. The medical apparatus according to claim 10, wherein the electrical signal generator is configured to apply the signals asynchronously with respect to a beating of the heart.

14. The medical apparatus according to claim 13, wherein the electrical signal generator is configured to apply the signals synchronously with respect to a beating of the heart.

15. A medical apparatus for tissue ablation, comprising:
a probe having a distal end, a proximal end and a length configured for insertion into a body of a patient and comprising an array of electrodes disposed successively along the length of the probe and configured to contact tissue within the body, the array having a proximal electrode at the proximal end of the probe and a distal electrode at distal end of the probe and a plurality of intermediary electrodes between the proximal and distal electrodes; and
an electrical signal generator configured to apply during a first period of time while the probe contacts a locus in the tissue, between one or more pairs of electrodes in the array, signals comprising a first sequence of bipolar pulses having a duration and an amplitude sufficient to cause irreversible electroporation (IRE) in the tissue between each pair of odd-even electrodes, the first sequence being applied beginning with a pair of electrodes comprising the proximal electrode and an electrode in the plurality of intermediary electrodes immediately adjacent the proximal electrode and continuing successively for each remaining pair of the electrodes in the array, and to apply during a second period of time while the probe remains in contact with the locus in the tissue, between even-odd electrodes in the array, signals comprising a second sequence of bipolar pulses having an amplitude sufficient to cause IRE in the tissue between each even-odd electrodes, the second sequence being applied beginning with a pair of electrodes comprising the electrode immediately adjacent proximal electrode and a successive immediately adjacent electrode of the plurality of intermediary electrodes and continuing successively for each remaining pair of the electrodes in the array.

16. The medical apparatus according to claim 15, wherein each of the plurality of sequences of bipolar pulses comprises pulses, the amplitude being at least 200 V, and the duration of each of the bipolar pulses being less than 20 µs.

17. The medical apparatus according to claim 15, wherein the electrical signal generator is configured to generate a plurality of pulse trains comprising the first and second sequences of bipolar pulses, wherein the pulse trains are separated by intervals in which the first and second sequences of bipolar pulses are not applied.

18. The medical apparatus according to claim 15, wherein the probe is configured to contact the tissue in a heart of the patient and to apply the first and second sequences of the bipolar pulses so as to ablate the tissue in the heart.

19. The medical apparatus according to claim 18, wherein the electrical signal generator is configured to apply the signals asynchronously with respect to a beating of the heart.

20. The medical apparatus according to claim 18, wherein the electrical signal generator is configured to apply the signals synchronously with respect to a beating of the heart.

21. The medical apparatus according to claim 15, wherein the probe comprises a plurality of temperature sensors adjacent to the array of electrodes, and wherein the electrical signal generator is configured to apply the first and second sequences of bipolar pulses responsively to a temperature measured by the temperature sensors.

22. The medical apparatus according to claim 15, wherein the electrical signal generator is further configured to apply the first and second sequences of the bipolar pulses between pairs of electrodes that are separated by at least one other electrode in the array, the amplitude of the bipolar pulses being sufficient to cause irreversible electroporation (IRE) in the tissue between the electrodes in the pairs.

23. A method for ablating tissue within a body of a patient, the method comprising:

inserting a probe having a distal end, a proximal end and a length into the body, wherein the probe comprises an array of electrodes disposed successively along the length of the probe and configured to contact the tissue, the array having a proximal electrode at the proximal end of the probe and a distal electrode at distal end of the probe and a plurality of intermediary electrodes between the proximal and distal electrodes; and applying between one or more pairs of the array of electrodes of the array, signals of first and second types in alternation, the signals of the first type comprising a first sequence of bipolar pulses having a duration and an amplitude sufficient to cause irreversible electroporation (IRE) in the tissue, the first sequence of bipolar pulses being applied to odd-even pairs of electrodes in the array during a first period of time while the probe contacts a locus in the tissue, the first sequence being applied beginning with a pair of electrodes comprising the proximal electrode and an electrode of the plurality of intermediary electrodes immediately adjacent the proximal electrode and continuing successively for each remaining pair of electrodes in the array, and a second sequence of bipolar pulses having a duration and an amplitude sufficient to cause IRE in the tissue between each even-odd pairs of electrodes in the array during a second period of time while the probe remains in contact with the locus, the second sequence being applied beginning with a pair of electrodes comprising the electrode immediately adjacent the proximal electrode and a successive immediately adjacent electrode of the plurality of intermediary electrodes and continuing successively for each remaining pair of electrodes in the array, and the signals of the second type comprising a radio-frequency (RF) signal having a power sufficient to thermally ablate the tissue contacted by the electrodes.

24. The method according to claim 23, wherein each of the plurality of sequences of bipolar pulses comprises pulses the amplitude is at least 200 V, and the duration of each of the bipolar pulses is less than 20 µs.

25. The method according to claim 23, wherein the RF signal has a frequency of between 350 and 500 kHz and an amplitude of between 10 and 200 V.

26. The method according to claim 23, wherein applying the signals of the first and second types comprises generating a each of the first and second sequences of bipolar pulses wherein the amplitude and the duration are selected, and configuring a network of multiple, mutually connected fast switches and slow relays to transmit the sequences of bipolar pulses to the plurality of electrodes.

27. The method according to claim 26, wherein applying the signals of the second type comprises applying a low-pass filter to convert the second sequences of pulses into the RF signal, thereby generating the signals of the second type.

28. The method according to claim 23, wherein applying the signals of the first type comprises applying sequences of bipolar pulses, wherein each sequence comprises a positive pulse and a negative pulse, and wherein applying signals of the second type comprises interleaving the signals of the second type between the positive and negative pulses of the sequences.

29. The method according to claim 23, wherein applying the signals of the first type comprises applying sequences of bipolar pulses, wherein each sequence comprises a positive pulse and a negative pulse, and wherein applying signals of the second type comprises interleaving the signals of the second type between successive sequences of the pulses.

30. The method according to claim 23, wherein applying the signals of the first and second types comprises applying a plurality of pulse trains, each pulse train comprising the signals of the first and second types, and separating the pulse trains by intervals in which the signals of the first and second types are not applied.

31. The method according to claim 23, and comprising measuring a temperature of the tissue using a plurality of temperature sensors adjacent to the plurality of electrodes, wherein applying the signals of the first and second types comprises controlling the signals of the first and second types responsively to the temperature measured by the temperature sensors.

32. The method according to claim 23, wherein inserting the probe comprises bringing the plurality of electrodes into contact with the tissue in a heart of the patient, and wherein applying the signals of the first and second types comprises ablating the tissue in the heart.

33. The method according to claim 32, wherein applying the signals of the first and second types comprises applying the signals of the first and second types asynchronously with respect to a beating of the heart.

34. The method according to claim 32, wherein applying the signals of the first and second types comprises applying the signals of the first and second types synchronously with respect to a beating of the heart.

35. A method for ablating tissue within a body of a patient, the method comprising:

inserting a probe having a length into the body, wherein the probe comprises an array of a plurality of electrodes disposed successively along the length of the probe and configured to contact the tissue, the array having a proximal electrode at a proximal end of the probe and a distal electrode at a distal end of the probe and a plurality of intermediary electrodes between the proximal and distal electrodes; and applying during a first period of time while the probe contacts a locus in the tissue, between odd-even pairs of electrodes in the array, signals comprising a first sequence of bipolar pulses having a duration and an amplitude sufficient to cause irreversible electroporation (IRE) in the tissue between each odd-even electrodes, the first sequence being applied beginning with a pair of electrodes comprising the proximal electrode and an electrode of the plurality of intermediary electrodes immediately adjacent the proximal electrode and continuing successively for each remaining pair of the electrodes in the array, and applying during a second period of time while the probe remains in contact with the locus in the tissue, between each even-odd electrodes in the array, signals comprising a second sequence of bipolar pulses having an amplitude sufficient to cause IRE in the tissue between each even-odd electrodes, the second sequence being applied beginning with a pair of electrodes comprising the electrode immediately adjacent the proximal electrode and a successive immediately adjacent electrode of the plurality of intermediary electrodes and continuing successively for each remaining pair of electrodes in the array.

36. The method according to claim 35, wherein each of the plurality of sequences of bipolar pulses comprises pulses, the amplitude being at least 200 V, and the duration of each of the bipolar pulses being less than 20 μs.

37. The method according to claim 35, wherein applying the signals of first and second types comprises applying a plurality of pulse trains comprising the first and second sequences of bipolar pulses, wherein the pulse trains are separated by intervals in which the bipolar pulses are not applied.

38. The method according to claim 35, wherein inserting the probe comprises bringing the electrodes into contact with the tissue in a heart of the patient, and wherein applying the signals of the first and second types comprises ablating the tissue in the heart.

39. The method according to claim 38, wherein applying the signals of the first and second types comprises applying the signals of the first and second types asynchronously with respect to a beating of the heart.

40. The method according to claim 38, wherein applying the signals comprises applying the signals of the first and second types synchronously with respect to a beating of the heart.

41. The method according to claim 35, and comprising measuring a temperature of the tissue using a plurality of temperature sensors adjacent to the plurality of electrodes, wherein applying the signals of the first and second types comprises controlling the signals of the first and second types responsively to the temperature measured by the temperature sensors.

42. The method according to claim 35, and further comprising applying the first and second sequences of the bipolar pulses between pairs of electrodes that are separated by at least one other electrode in the array, the amplitude of the bipolar pulses being sufficient to cause irreversible electroporation (IRE) in the tissue between the electrodes in the pairs.

* * * * *